United States Patent
Sun et al.

(10) Patent No.: US 9,975,818 B2
(45) Date of Patent: May 22, 2018

(54) PROCESS FOR MAKING BIOBASED ISOPRENE

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignees: Archer Daniels Midland Company, Decatur, IL (US); Washington State University, Pullman, WA (US)

( * ) Notice: Subject to any disclaimer, the term of this patent is extended or adjusted under 35 U.S.C. 154(b) by 0 days. days.

(21) Appl. No.: 14/683,252

(22) Filed: Apr. 10, 2015

(65) Prior Publication Data
US 2015/0239803 A1 Aug. 27, 2015

Related U.S. Application Data (63) Continuation-in-part of application No. PCT/US2013/062784, filed on Oct. 1, 2013, and a continuation-in-part of application No. PCT/US2013/063968, filed on Oct. 9, 2013, and a continuation-in-part of application No. PCT/US2013/063971, filed on Oct. 9, 2013, and a continuation-in-part of application No. PCT/US2013/067031, filed on Oct. 28, 2013.

(60) Provisional application No. 61/720,433, filed on Oct. 31, 2012, provisional application No. 61/737,312, filed on Dec. 14, 2012, provisional application No. 61/836,188, filed on Jun. 18, 2013, provisional application No. 61/844,957, filed on Jul. 11, 2013.

(51) Int. Cl.
*C07C 2/86* (2006.01)
*C08F 36/08* (2006.01)
*C07C 1/207* (2006.01)
*C07C 1/24* (2006.01)
*C07C 2/10* (2006.01)

(52) U.S. Cl.
CPC ............ *C07C 2/867* (2013.01); *C07C 1/2074* (2013.01); *C07C 1/24* (2013.01); *C07C 2/10* (2013.01); *C08F 36/08* (2013.01); *C07C 2521/06* (2013.01); *C07C 2523/06* (2013.01); *Y02P 20/52* (2015.11)

(58) Field of Classification Search
CPC .. C07C 2/867; C07C 1/20; C07C 1/24; C07C 1/2078; C07C 11/09; C07C 11/18; C07C 2523/06; C07C 2521/06; C08F 36/08; C08F 236/08
See application file for complete search history.

(56) References Cited

U.S. PATENT DOCUMENTS

2006/0161035 A1* 7/2006 Kalnes ...................... C07C 1/20
585/639

OTHER PUBLICATIONS

Sun et al., J. Amer. Chem. Soc. 133 (2011) 11096-11099.*

* cited by examiner

*Primary Examiner* — Roberto Rabago
(74) *Attorney, Agent, or Firm* — William B. Miller (57) ABSTRACT

Processes are described for making biobased isoprene, wherein a biobased isobutene prepared from acetic acid in the presence of a catalyst is combined with a formaldehyde source to form a reaction mixture, and the reaction mixture is reacted to yield biobased isoprene. In certain embodiments, methyl-tert-butyl ether prepared by reacting the same biobased isobutene with methanol serves as a formaldehyde source, being oxidatively cracked to produce formaldehyde as well as isobutene for being converted to the biobased isoprene.

11 Claims, 5 Drawing Sheets

PROCESS FOR MAKING BIOBASED ISOPRENE

CROSS-REFERENCE TO RELATED APPLICATIONS

Technical Field

The present invention relates to methods of making isoprene from isobutene or from methyl tert-butyl ether (MTBE).

BACKGROUND ART

As background, conventionally isoprene has been recovered from pyrolysis gasoline in naphtha cracking to produce ethylene, by a series of fairly capital intensive steps. Initially cyclopentadiene is removed from the pyrolysis gasoline by dimerization and distillation. Subsequently, pipirylenes are separated out by superfractionation, and the isoprene (at 10 to 20% of the pyrolysis gasoline) is then recovered by extractive distillation using a solvent. In recent years, however, with the availability of abundant, inexpensive natural gas, ethylene has increasingly been produced using lighter feedstocks for the steam crackers so that pyrolysis gasoline production has declined.

A number of other petroleum processing-based or -dependent routes to isoprene have been developed as well. As summarized in WO 2012/038247 A1 by Vermeiren et al., "Production of Isoprene from Iso-Butanol" ("WO '247"), isoprene can be produced by the isolation of isoamylenes from refinery and petroleum cuts and the subsequent hydrogenation of the isoamylenes over an iron oxide catalyst promoted with potassium compounds. Isoprene can also be produced from isopentane by a double dehydrogenation. In another known process, isoprene is produced by a Prins condensation of a $C_4$ olefin feed with an aldehyde, typically formaldehyde, with the $C_4$ olefin feed commonly including isobutene or one or more isobutene precursors such as an alkyl-t-butyl ether under conditions which will provide isobutene. The isobutene reacts with formaldehyde to give 4,4-dimethyl-m-dioxane which decomposes to provide the desired isoprene product.

WO '247 reports a number of examples of processes of this general character. For example, U.S. Pat. No. 4,511,751 describes a process wherein isobutene and/or tertiary butanol and a formaldehyde source are fed, together with water, into an acidic aqueous solution continuously or intermittently while maintaining the reaction pressure in an adequate range and at the same time distilling off the isoprene product and unreacted starting materials, together with water, from the reaction zone. U.S. Pat. No. 4,593,145 is cited for describing a process for producing isoprene, characterized in that an alkyl-t-butyl ether (e.g., methyl-t-butyl ether (MTBE) or ethyl-t-butyl ether (ETBE) as are still commercially manufactured and extensively used as antiknock fuel additives) and a formaldehyde source are fed, together with water, into an acidic aqueous solution continuously or intermittently while maintaining the reaction pressure in an adequate range and at the same time distilling off the product isoprene, unreacted starting materials, isobutene and tertiary butanol, together with water, from the reaction zone. Other cited examples include EP 106323, EP 1614671, EP 2157072, GB 1370899 and U.S. Pat. No. 3,972,955.

It is also known to produce isoprene from tertiary alkyl ethers (such as MTBE) and an oxygen source by a catalytic process. For example, in U.S. Pat. No. 3,574,780, isoprene is produced by passing a mixture of MTBE and air over a mixed oxide catalyst, cracking the MTBE to isobutene and methanol, oxidizing the methanol to formaldehyde and then reacting the isobutene and formaldehyde to produce isoprene. Other references supply isobutene and methanol separately. The methanol is oxidized to formaldehyde alongside methanol generated from the cracking of MTBE, and the formaldehyde so formed reacts with the supplied isobutene plus that isobutene generated from the cracking of MTBE. Still other references supply isobutene and methanol directly rather than generating the same by cracking MTBE, oxidizing the methanol to formaldehyde with an oxygen source in the presence of an oxidation catalyst and then reacting the formaldehyde thus formed with the isobutene feed.

While there are thus a number of known methods for producing isoprene, each of these methods has shared the disadvantage of being dependent at least to some extent on petroleum-based or -derived materials and on petroleum processing economics.

In recognition of the desirability of a renewable source-derived isoprene, the WO'247 application provides a process for making isoprene using isobutanol, especially isobutanol produced using biomass as a primary feedstock, as an isobutene precursor. More particularly, at least 25 mole percent of the carbon implicated in the isobutanol is obtained from renewable resources, whether by the base-catalyzed Guerbet condensation of methanol with ethanol and/or propanol, by hydrogenation of synthesis gas from the gasification of biomass and/or by an amino acid biosynthetic route from carbohydrates from biomass. The at least partly bioderived isobutanol in turn provides at least 10 up to 100 percent of the isobutene, with the balance being provided by t-butanol, another isobutene precursor such as MTBE or from fresh isobutene.

SUMMARY OF THE INVENTION

As mentioned previously, since our '433 and '312 applications provide means by which a biobased isobutene may be viably produced, in one aspect the present invention concerns a process for making isoprene wherein a biobased isobutene prepared as described in either of these applications is combined with a formaldehyde source to form a reaction mixture, and the reaction mixture is reacted to provide a product mixture, then isoprene is recovered from the product mixture. In a preferred embodiment, the reaction mixture is reacted while distilling away a mixture comprising produced isoprene, water, unreacted starting materials and other low boiling components.

Since MTBE may also be used to produce isoprene according to certain conventionally known processes, in another aspect the present invention concerns a process for making isoprene wherein MTBE produced from a biobased isobutene in the manner of the '188 application is cracked to provide isobutene and methanol, methanol from the MTBE is oxidized to provide a source of formaldehyde, and the formaldehyde and isobutene are combined to form a reaction mixture. The reaction mixture is reacted to provide a product mixture, then isoprene is recovered from the reaction mixture. Again, in a preferred embodiment, the reaction mixture is reacted while distilling away a mixture comprising produced isoprene, water, unreacted starting materials and other low boiling components.

In yet another aspect, the present invention concerns a process wherein both biobased isobutene and MTBE prepared from biobased isobutene are combined with a formaldehyde source to form a reaction mixture, and the reaction mixture is reacted to provide a product mixture, then isoprene is recovered from the product mixture. In a preferred embodiment, the reaction mixture is reacted while distilling away a mixture comprising produced isoprene, water, unreacted starting materials and other low boiling components.

In yet another aspect, wholly biobased butyl rubber is provided by copolymerizing biobased isobutene prepared as described in either of the '433 and '312 applications with biobased isoprene prepared using additional of the same biobased isobutene and a wholly biobased formaldehyde source and/or using a wholly biobased MTBE prepared in the manner of the '188 application.

DESCRIPTION OF EMBODIMENTS

Figure 1:
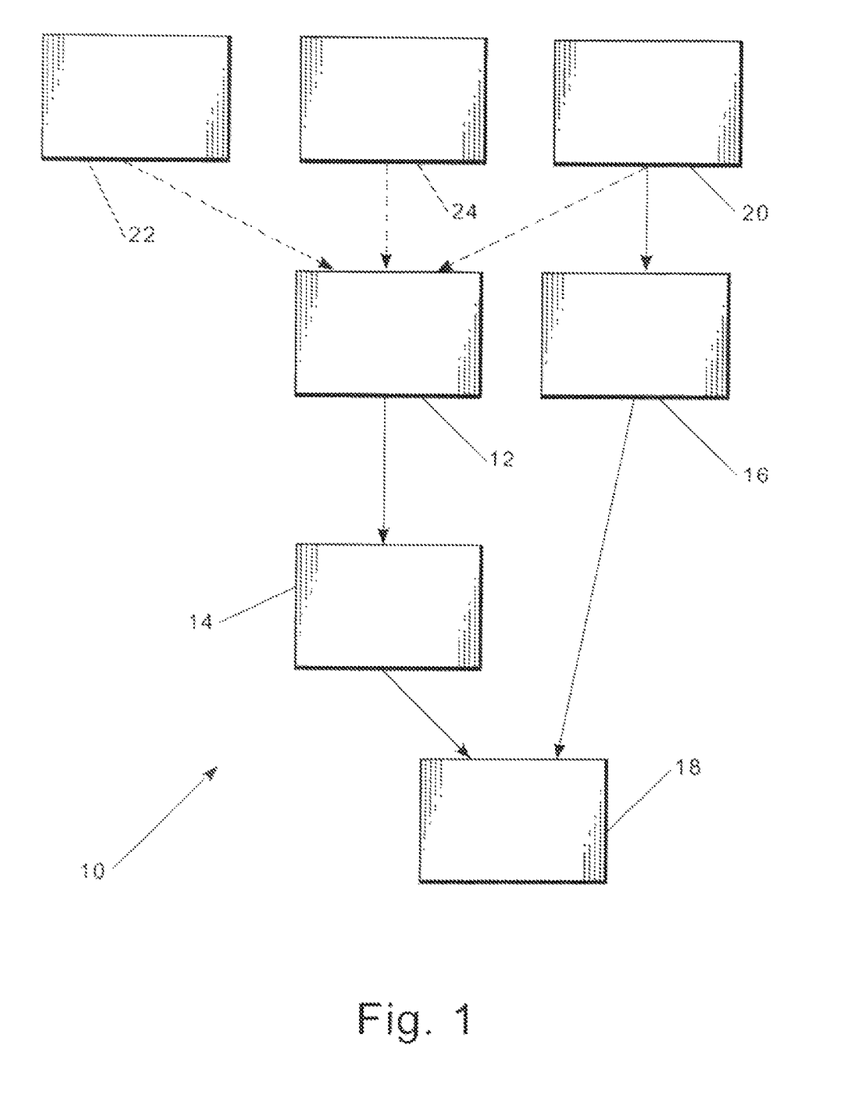
FIG. 1 schematically depicts a process for making isoprene using biobased isobutene prepared from acetic acid.

Referring now to FIG. 1, a process embodiment 10 according to a first aspect is schematically illustrated wherein acetic acid 12 is converted to isobutene 14 in the presence of a catalyst, particularly, a $Zn_xZr_yO_z$ mixed oxide catalyst, and the isobutene 14 is then reacted with formaldehyde 16 to produce an isoprene product 18.

Where the methanol 20 from which the formaldehyde 16 is obtained (by oxidation according to any of the commercially-practiced or known methods) is wholly biobased in origin, being derived from biological carbon sources rather than from methane from natural gas, for example, a wholly biobased isoprene 18 may be obtained.

Parenthetically, by "biobased", we mean those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

Figure 5:
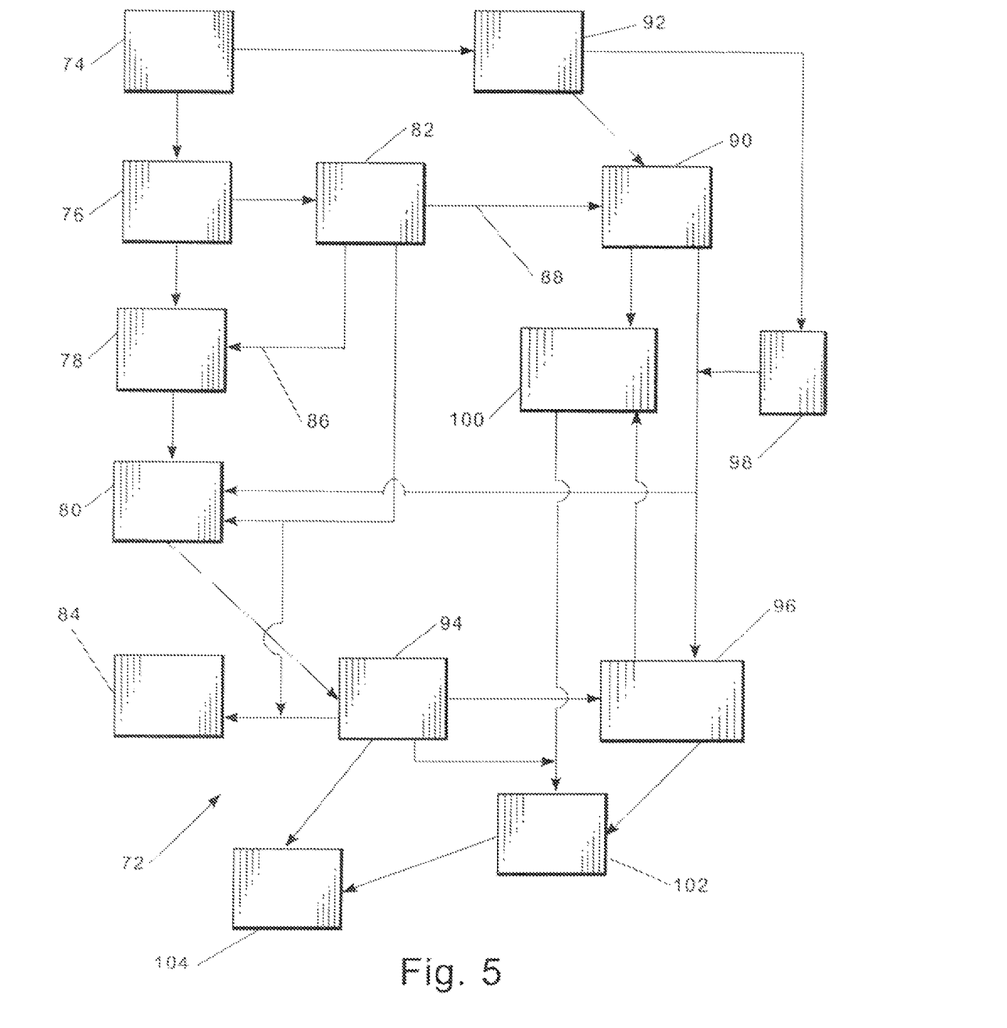
FIG. 5 schematically depicts a particular embodiment of a process of the type shown in FIG. 4.

Acetic acid 12 can be obtained by various methods from a number of starting materials, which in turn permits a number of integrated processes to be considered for producing the isoprene 18 with improved utilization of renewable resources. An example is schematically shown in FIG. 5, discussed more fully below.

For example, acetic acid can be produced from a source of five and six carbon sugars 22 by fermentation. U.S. Pat. No. 6,509,180 and U.S. Pat. No. 8,252,567 seek to improve upon known processes for making ethanol and butanol/hexanol, respectively, by means including the fermentation of five and six carbon sugars into acetic acid. In U.S. Pat. No. 6,509,180, the acetic acid is esterified to form an acetate ester which may then be hydrogenated (using hydrogen from, e.g., steam reforming of natural gas, electrolysis of water, gasification of biomass or partial oxidation of hydrocarbons generally) to ethanol. In U.S. Pat. No. 8,252,567, the ethanol formed in this manner can be used to make butanol and hexanol, by subjecting the ethanol with acetate, acetic acid or mixtures thereof to an acidogenic fermentation using, for example, species of the bacteria *Clostridium* (*Clostridium kluyveri* is mentioned), to produce butyrate, butyric acid, caproate, caproic acid or mixtures thereof. These materials then in turn are acidified to convert butyrate and caproate to butyric acid and caproic acid, the butyric and caproic acids are esterified and then the butyric and caproic acid esters undergo reduction by hydrogenation, hydrogenolysis or reduction by carbon monoxide to provide butanol and ethanol.

As related in these two patents and as is well known to those skilled in the fermentation art, the fermentation of five and six carbon sugars to form acetic acid can be accomplished by various organisms. More particularly, homoacetogenic microorganisms are able through fermentation to produce acetic acid with 100% carbon yield; these microorganisms internally convert carbon dioxide to acetate, in contrast to a process for producing ethanol from sugars obtained from biomass, wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. No. 4,935,360; U.S. Pat. No. 8,236,534; U.S. Pat. No. 4,513,084; U.S. Pat. No. 4,371,619 and U.S. Pat. No. 4,506,012; both one-step fermentation processes from the sugars to acetic acid, acetates or both are disclosed, as well as two-step processes involving a first fermentation to lactic acid (by *lactobacillus* or known methods of homolactic fermentation, preferably) followed by a second fermentation to convert lactic acid to acetic acid, for example, using *Clostridium formicoaceticum*.

Any of the known fermentation methods may, in short, be used to produce acetic acid 12 for conversion to isobutene 14 as shown in FIG. 1, but homoacetogenic fermentation methods are considered preferable in that carbon dioxide is not produced as a byproduct—the carbon dioxide represents a yield loss from the overall process to make isobutene and as a greenhouse gas is undesirable particularly in the context of a process to make a needed product more sustainably from renewable resources.

As well or in the alternative, the acetic acid feedstock 12 can be made from ethanol 24, according to any of several known methods employing oxidative fermentation with acetic acid bacteria of the genus *Acetobacter*.

As well or in the alternative, the acetic acid feedstock 12 can be made from methanol 20, through combination with carbon monoxide according to the most industrially used route for making acetic acid, for example, in the presence of a catalyst under conditions effective for the carbonylation of methanol. A variety of carbonylation catalysts are known in this regard, see, for example, U.S. Pat. No. 5,672,743; U.S. Pat. No. 5,728,871; U.S. Pat. No. 5,773,642; U.S. Pat. No. 5,883,289; U.S. Pat. No. 5,883,295.

The wholly biobased isobutene 14 enabled by the process of the '312 application and formaldehyde 16 may be reacted as schematically shown in FIG. 1 to produce isoprene 18 according to any of a number of known methods, including but not limited to those methods summarized above and described more fully in the WO'247 application; U.S. Pat. No. 4,511,751; U.S. Pat. No. 4,593,145; EP 106323; EP 1614671; EP 2157072; GB 1370899; U.S. Pat. No. 3,972,955 and the various prior isoprene manufacturing methods summarized in each of these. Again, using methanol 20 derived from biological carbon sources to prepare the formaldehyde 16, a wholly biobased isoprene 18 is enabled.

In this regard, with increasing concerns for the abatement of greenhouse gases such as carbon dioxide in recent years, a substantial amount of work has been reported on methods to convert carbon dioxide to methanol, see, for example, Wesselbaum et al., "Hydrogenation of Carbon Dioxide to Methanol by Using a Homogeneous Ruthenium-Phosphine Catalyst", *Angew. Chem. Int. Ed.*, vol. 51, pp 7499-7502 (2012); Ma et al., "A Short Review of Catalysis for $CO_2$ Conversion", *Catalysis Today*, vol. 148, pp 221-231 (2009); Borodko et al., "Catalytic Hydrogenation of Carbon Oxides—a 10-Year Perspective", *Applied Catalysis A: General*, vol. 186, pp 355-362 (1999); and U.S. Pat. No. 8,212,088 to Olah et al., "Efficient and Selective Chemical Recycling of Carbon Dioxide to Methanol, Dimethyl Ether and Derived Products" and the various additional references cited in each of these. Those skilled in the art will thus be well-acquainted with processes and associated catalysts for producing methanol 20 from carbon dioxide, carbon monoxide and hydrogen variously obtained from the anaerobic digestion of biomass through methane, from electrolysis of water using energy from geothermal sources, by electrolytic cleavage of carbon dioxide to produce carbon monoxide and water and so forth.

Figure 2:
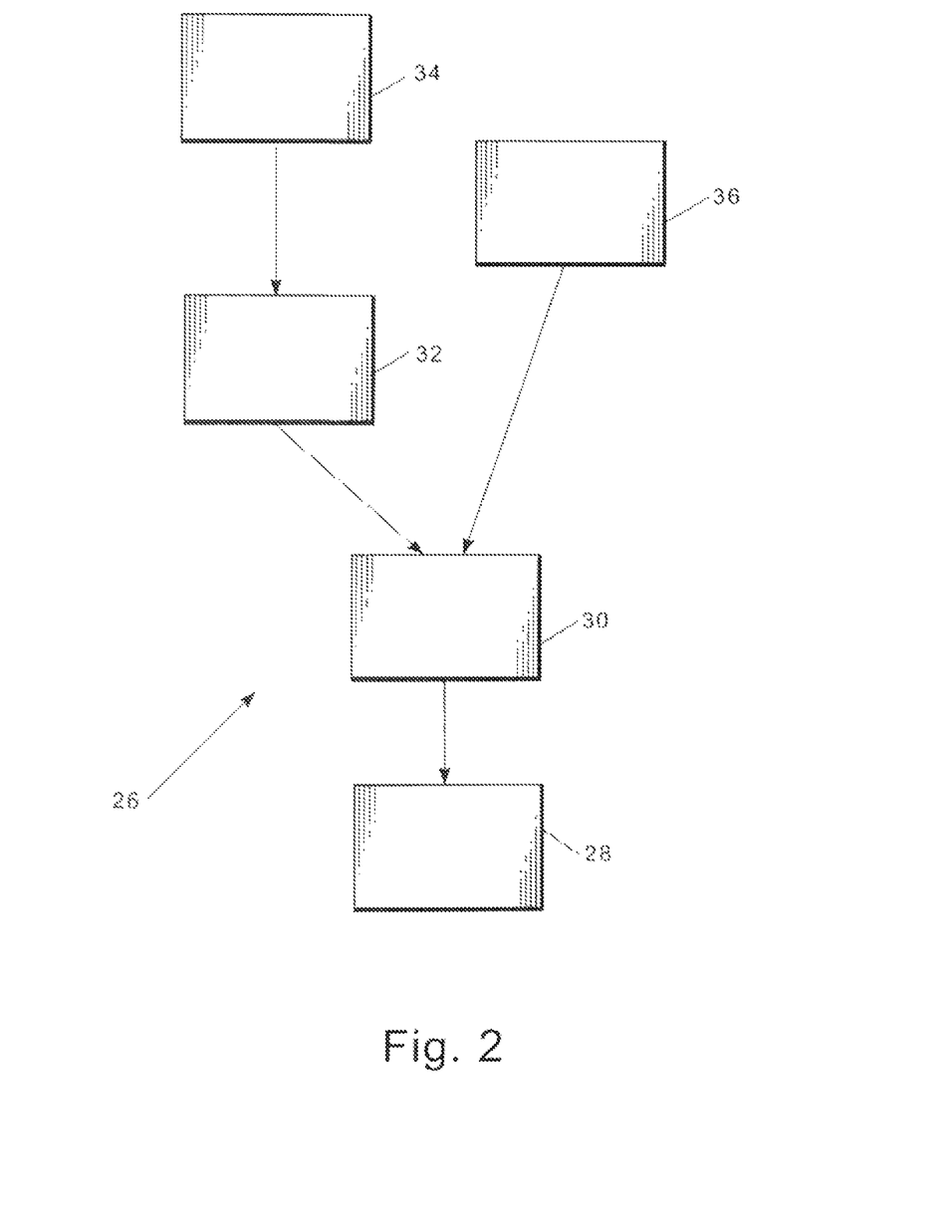
FIG. 2 schematically depicts a process for making isoprene from MTBE prepared from biobased isobutene.

Turning now to FIG. 2, a process embodiment 26 is schematically shown for making isoprene 28 from a biobased methyl-t-butyl ether (MTBE) 30 according to a second aspect of the present invention. It should be noted, parenthetically, that for avoiding possible confusion different reference numbers are employed in FIG. 2 as opposed to FIG. 1, though for example the isoprene 28 is desirably substantially the same as isoprene 18 in the process 10 of FIG. 1, being of the same essential quality, character and functionality as isoprene obtained from conventional petroleum-based processing. The biobased MTBE 30 can be combined with air and converted to isoprene as described in U.S. Pat. No. 3,574,780, through passing a mixture of MTBE 30 and air over a mixed oxide catalyst, cracking the MTBE 30 to isobutene and methanol, oxidizing the methanol to formaldehyde and then reacting the isobutene and formaldehyde to produce the isoprene 28.

The biobased MTBE 30 in turn is produced by a process as described in the '188 application, from isobutene 32 produced from acetic acid 34 produced as described in the '312 application (using a catalyst, particularly a $Zn_xZr_yO_z$ mixed oxide catalyst, and especially a $Zn_xZr_yO_z$ mixed oxide catalyst made as described in the '433 application) and from methanol 36.

In alternative embodiments not specifically illustrated in the schematic, those skilled in the art will appreciate that additional methanol 36 (beyond that used to form the MTBE 30 and produced therefrom as described in U.S. Pat. No. 3,574,780) and additional isobutene 32 can be supplied alongside the MTBE 30 to make the isoprene 28. As well, isobutene 32 and methanol 36 can be supplied directly for oxidation and without a separate step of forming the MTBE 30; the methanol is oxidized to formaldehyde with an oxygen source in the presence of an oxidation catalyst, and the formaldehyde is then reacted with the isobutene feed preferably using the same catalyst to produce the isoprene 28.

Figure 3:
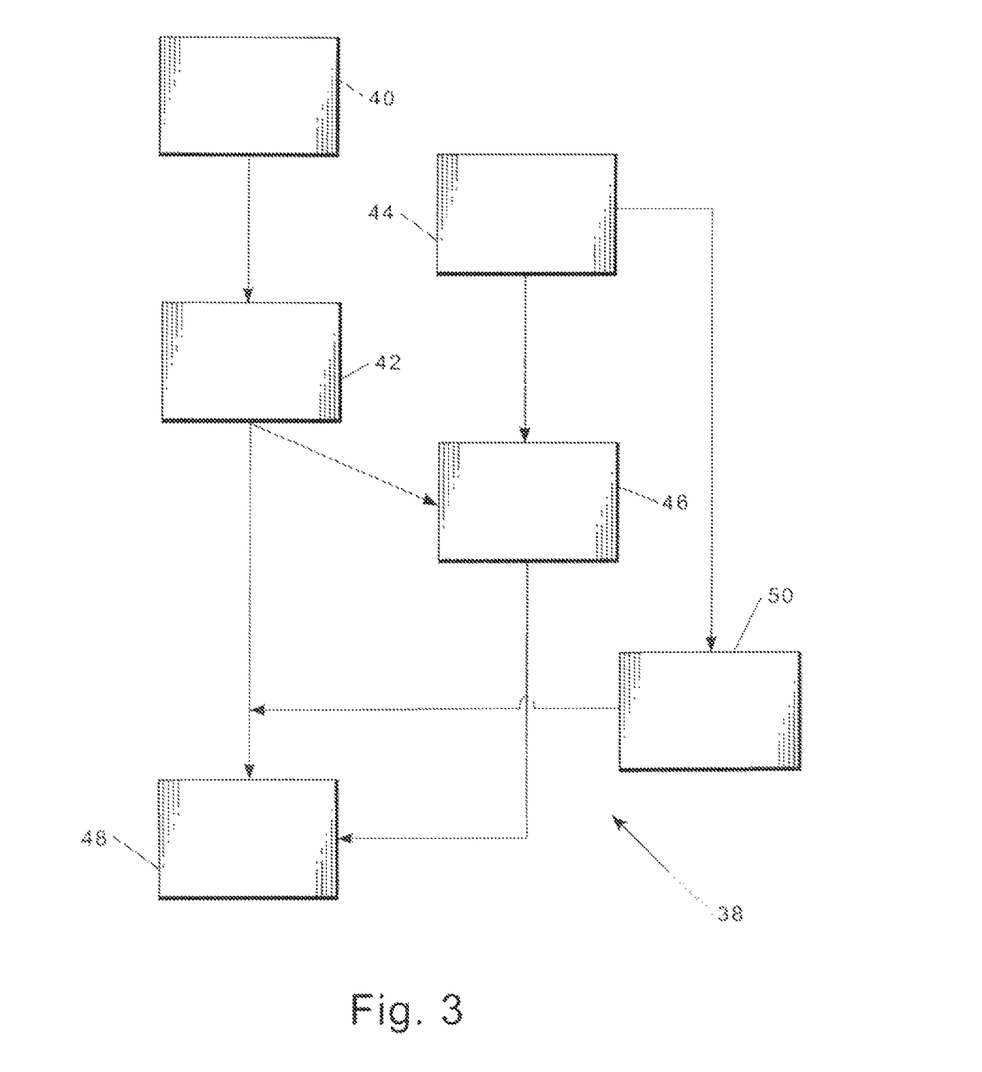
FIG. 3 schematically depicts a process combining the processes of FIGS. 1 and 2, for making isoprene using both biobased isobutene and MTBE prepared from biobased isobutene according to the third aspect described above.

In a still further process embodiment schematically shown in FIG. 3, a process 38 is shown in which acetic acid 40 is converted to isobutene 42 as described in the '312 application. A portion of the isobutene 42 is combined with a corresponding portion of methanol 44 to produce MTBE 46, and at least a portion of the MTBE 46 is converted to isoprene 48 by cracking the MTBE to isobutene and methanol, oxidizing the methanol to formaldehyde and causing the isobutene and formaldehyde to react to form the desired isoprene. The isobutene and formaldehyde thus derived are supplemented in the process 38 by additional isobutene 42 and by formaldehyde 50 separately produced from additional methanol 44 according to known processes.

Figure 4:
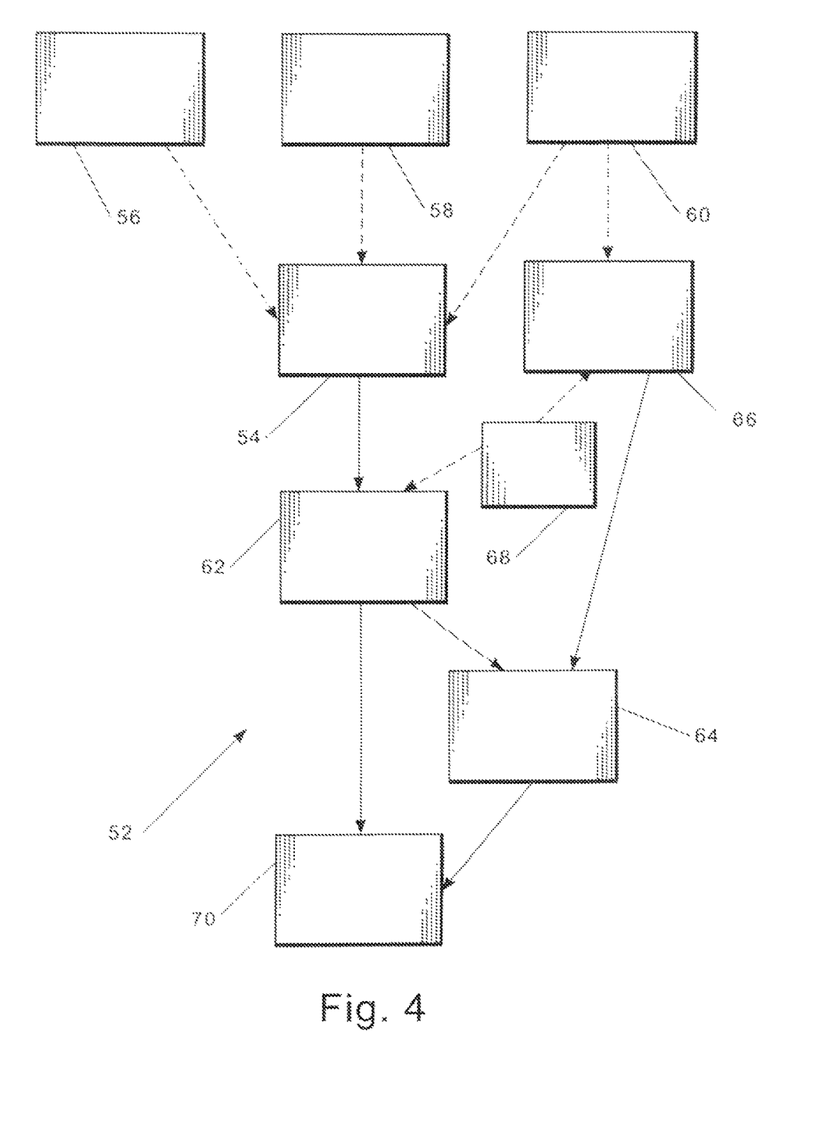
FIG. 4 schematically depicts a process for making a wholly biobased butyl rubber using biobased isobutene and using isoprene prepared from the biobased isobutene and from formaldehyde made from methanol, according to the fourth aspect of the invention described above.

Turning now to FIG. 4, because wholly biobased isobutene can be made as described in the '312 application and wholly biobased isoprene made by a process as described herein (the processes schematically shown in FIGS. 1-3 being examples), a wholly biobased butyl rubber can be made. Processes for the copolymerization of isobutene and isoprene are well known and have been commercially practiced for years, though some recent examples of published patent applications and/or patents for processes for making such copolymers include EP 1215241B1, EP 1449859A1, EP 1426387B1, U.S. Pat. No. 7,041,760 and U.S. Pat. No. 7,851,577. For purposes of the present invention, any known process for copolymerizing isobutene and isoprene may be used, however.

In the process embodiment 52 schematically shown in FIG. 4, acetic acid 54 (whether obtained by fermentation of five and/or six-carbon sugars 56, from ethanol 58 by oxidative fermentation, from methanol 60 by carbonylation or a combination of these, all as described above) is converted to wholly biobased isobutene 62 by a process as described in the '312 application and summarized below. Wholly biobased isoprene 64 is prepared from formaldehyde 66, with the formaldehyde 66 in turn being prepared by oxidizing a portion of the methanol 60, through cracking of MTBE 68 prepared from wholly biobased isobutene according to the '188 application or by a combination of these synthetic methods as previously described. The wholly biobased isobutene 62 and wholly biobased isoprene 64 are then copolymerized to provide a wholly biobased butyl rubber product 70 using any of the known processes for accomplishing the copolymerization.

Turning now finally to FIG. 5, a non-limiting example 72 is shown of an integrated process for making biobased alternatives to one or more of the valuable products isobutene, isoprene, MTBE and ETBE which have all heretofore been made at least in part through petroleum processing, through use of the core acetic acid to isobutene conversion described in the '312 application. While one example 72 is detailed herein, those skilled in the art and familiar with the known processes for producing methanol, ethanol and acetic acid (some of which have been mentioned above or will be mentioned below) and with the known methods by which the "building block" gases carbon dioxide, carbon monoxide and hydrogen may be generated and used to make one or more of the same methanol, ethanol and acetic acid feeds will undoubtedly be able to conceive of a number of other integrated process schemes which all make use of the core acetic acid to isobutene conversion, but differ in the precise manner or extent to which carbon dioxide, carbon monoxide and hydrogen gases are optimally used.

Nevertheless, in the particular integrated process embodiment 72 shown schematically in FIG. 5, biomass 74 can be a source of five and six carbon sugars 76, which can undergo a fermentation step 78 as earlier mentioned to make acetic acid 80. Some of the sugars can be fermented according to known methods for fermentation of five- and six-carbon sugars to make ethanol 82, with the ethanol 82 in turn being useful for making ETBE 84 by conventionally practiced etherification process technology and/or for making acetic acid 80 as described above. Carbon dioxide generated as a byproduct in the ethanol fermentation can variously be used as suggested by stream 86 in a homoacetogenic fermentation 78 for making the acetic acid 80, or can be used as suggested by stream 88 to make methanol 90. This carbon dioxide (that is, in streams 86 and 88) can be combined for either or both purposes with carbon dioxide from a variety of other sources, for example, with carbon dioxide captured from industrial emissions, generated in the combustion of fossil fuels, sequestered in underground reservoirs or contained in biosynthesis gas 92 from the combustion, gasification or partial oxidation of biomass 74 or of a non-fermentable biomass fraction generated in a fractionation of the biomass 74 to produce fermentable sugars 76. In the context of a biomass fractionation process as described in any of several commonly-assigned, copending applications, namely, published applications WO 2011/097065 and WO 2011/097075 both to Binder et al., as well as Patent Cooperation Treaty Applications Ser. No. PCT/US2012/056593, filed Sep. 21, 2012 for "$C_1$-$C_2$ Organic Acid treatment of Lignin Biomass to Produce Acylated Cellulosic Pulp, Hemicellulose, Lignin and Sugars and Fermentation of the Sugars", and PCT/US2012/056593, filed Apr. 10, 2013 for "Liquid-Liquid Separation of Lignocellulosic Biomass to Produce Sugar Syrups and Lignin Fractions", the non-fermentable biomass fraction would include lignin.

The methanol 90 can variously be combined with biobased isobutene 94 (from acetic acid 80) for forming the MTBE fuel additive 96, combined with carbon monoxide 98 from biosynthesis gas 92 (or from the electrolytic cleavage of $CO_2$ from any of the sources mentioned above in connection with the generation of the methanol 90) to produce acetic acid 80 and/or used to make formaldehyde 100, with the latter being useful for combining with isobutene 94 to make isoprene 102. The isoprene 102 and isobutene 94 can then be used to make a butyl rubber product 104, if desired. As well, where demand for MTBE is not as strong as demand for isobutene, for isoprene and/or for butyl rubber or other polymer products that may be conventionally made using the isobutene and isoprene, MTBE 94 can be oxidatively cracked to produce additional of the formaldehyde 100 and isobutene 94.

The acetic acid 80 is converted to isobutene 94 as taught in the '312 application, preferably using a $Zn_xZr_yO_z$ mixed oxide catalyst. In one embodiment, the $Zn_xZr_yO_z$ mixed oxide catalyst can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2 \cdot 6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

The nanosized $Zn_xZr_yO_z$ mixed oxide catalysts made by a hard template method are further described by Sun et al., in "Direct Conversion of Bio-ethanol to Isobutene on Nanosized $Zn_xZr_yO_z$ Mixed Oxides with Balanced Acid-Base Sites", Journal of the American Chemical Society, vol. 133, pp 11096-11099 (2011), along with findings related to the character of the mixed oxide catalysts formed thereby and the performance of the catalysts for the ethanol to isobutene conversion, given certain Zn/Zr ratios, residence times and reaction temperatures.

Alternatively, the $Zn_xZr_yO_z$ mixed oxide catalysts may be made as described in the '433 application, by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template or incipient wetness methods) are characterized by a Zn/Zr ratio (x:y) of from 1:100 to 10:1, preferably from 1:30 to 1:1, especially 1:20 to 1:5, and still more preferably 1:12 to 1:10.

Parenthetically, in the present application where any range of values is given for any aspect or feature of the mixed oxide catalysts or any process described for using the mixed oxide catalysts, the given ranges will be understood as disclosing and describing all subranges of values included within the broader range. Thus, for example, the range of 1:100 to 10:1 will be understood as disclosing and describing not only the specific preferred and more preferred subranges given above, but also every other subrange including a value for x between 1 and 10 and every other subrange including a value for y between 1 and 100.

The catalysts made by the alternative, incipient wetness method are consistent in their particle size with the catalysts described in the Jacobsen et al. article, namely, comprising aggregates of less than 10 nm-sized particles with a highly crystalline structure. The Zn oxide component is again highly dispersed on the Zr oxide component.

In certain embodiments, the $Zn_xZr_yO_z$ mixed oxide catalysts are characterized as low sulfur catalysts, containing less than 0.14 percent by weight of sulfur. In the '433 application, it was reported in this regard that catalysts made by the incipient wetness method would desirably be substantially sulfur-free, preferably including less than 0.01 percent by weight of sulfur and more preferably including less than 0.001 weight percent of sulfur. It was postulated that the reduced sulfur content enabled by the incipient wetness method as compared to the hard template method contributed significantly to the much improved stability observed for the incipient wetness method catalysts of the '433 application for the ethanol to isobutene process.

In the context of a process for converting acetic acid to isobutene, however, as mentioned in the '312 application, in at least some embodiments and under certain process conditions some sulfur does appear to be beneficial, though as just indicated, it is expected that the amount of sulfur will preferably be such that the catalysts are characterized as low sulfur catalysts. Such low sulfur catalysts are most readily made by the incipient wetness method described briefly above and in greater detail in the '433 application.

In principle, provided the zinc and zirconium compounds and solids in these embodiments have a sufficiently low sulfur content in order to produce a low sulfur content when combined according to the incipient wetness method, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. As exemplified in the '312 application, low sulfur catalysts can also be made by the incipient wetness method starting with zinc and zirconium compounds that are sulfur-free or substantially sulfur-free, then doping in a desired sulfur content into the $Zn_xZr_yO_z$ mixed oxide catalysts used in certain embodiments of the acetic acid to isobutene process of the '312 application.

The conditions and times for the drying and calcining steps of an incipient wetness preparation will depend, of course, on the particular zinc and zirconium materials and solvent used, but in general terms, the drying step can be accomplished in a temperature range of from 60 degrees Celsius to 200 degrees Celsius over at least 3 hours, while the calcination can take place at a temperature of from 300 degrees Celsius to 1500 degrees Celsius, but more preferably a temperature of from 400 to 600 degrees Celsius is used. The calcination time can be from 10 minutes to 48 hours, with from 2 to 10 hours being preferred.

In still other embodiments, low sulfur catalysts as described could be prepared by a hard template method as described in the Jacobsen et al. publication, except that a suitably very low sulfur content carbon is used for the hard template to realize a low sulfur content in the finished catalyst.

In certain embodiments described in the '312 application, the acetic acid to isobutene process can be conducted continuously in the gas phase, using a fixed bed reactor or flow bed reactor. The reaction temperature may be in a range from 350 to 700 degrees Celsius, preferably, in a range from 400 to 500 degrees Celsius, and the WHSV can be in a range from 0.01 $hr^{-1}$ to 10 $hr^{-1}$, preferably from 0.05 $hr^{-1}$ to 2 $hr^{-1}$. Acetic acid/water solutions with steam to carbon ratios from 0 to 20, preferably from 2 to 5 can be used to provide acetic acid to the catalyst. An inert carrier gas, such as nitrogen, can be used.

The production of the more stable mixed oxide catalysts of the '433 application and the use of mixed oxide catalysts to convert both of ethanol and acetic acid to isobutene are demonstrated for purposes of illustration in the following non-limiting examples:

Example 1

Commercial zirconium hydroxide was dried at 120 degrees Celsius for more than 5 hours. Calculated amounts of $Zn(NO_3)_2$ (from Sigma-Aldrich, more than 99.8 percent purity) were dissolved in water to form a series of clear solutions. Dried zirconium hydroxide (also from Sigma-Aldrich, more than 99.8 percent purity) was then mixed with the solutions in turn by incipient wetness, in order to form wet powders impregnated with Zn in certain proportions to the zirconium in the form of the dried zirconium hydroxide powder. The wetted powders were then dried at 80 degrees Celsius for 4 hours, followed by calcination at 400 degrees Celsius for 2 hours and at 600 degrees Celsius for 3 hours to obtain a series of $Zn_xZr_yO_z$ catalysts.

Ethanol to isobutene runs were conducted with the catalysts thus prepared in a fixed-bed stainless steel reactor, having an inside diameter of 5 millimeters. A given amount of catalyst was packed between quartz wool beds. A thermocouple was placed in the middle of the catalyst bed to monitor the reaction temperatures. Before beginning the reaction, the catalyst beds were first pretreated by flowing 50 ml/minute of nitrogen at 450 degrees Celsius through the catalyst over a half hour, then a mixture of ethanol/water at steam to carbon ratios from 1 to 5 was introduced into an evaporator at 180 degrees Celsius by means of a syringe pump and carried into the reactor by the flowing nitrogen carrier gas. Meanwhile, the product line was heated to in excess of 150 degrees Celsius before a cold trap, to avoid condensing the liquid products in the product line.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

An ethanol/water solution (steam to carbon ratio of 2.5) was then supplied by flowing $N_2$ to the reactor at a weight hourly space velocity (WHSV) of 0.95 $hr^{-1}$. The ethanol concentration was 15.1 percent by weight, and the reaction temperature was 450 degrees Celsius. Ethanol conversion was 100% throughout, and isobutene selectivity declined by less than 2 percent over 200 hours on stream for the series of catalysts prepared as described.

Thermogravimetric and differential scanning calorimetry analysis of the recovered, spent catalysts showed only about 0.7 weight percent of coke after 207 hours onstream.

Example 2

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst.

An acetic acid to isobutene process was conducted with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 µm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

A consistent product of about 5 percent by weight of methane, about 10 percent by weight of acetone, about 33 percent by weight of carbon dioxide and more than about 50 percent by weight of the desired isobutene product was obtained; in contrast to the ethanol to isobutene process using these same $Zn_xZr_yO_z$ mixed oxide catalysts in Example 1, no ethylene or propylene was produced. The catalyst showed very high stability over the full duration of the run, with no signs of observable deactivation after more than 1400 minutes of time-on-stream operation.

Examples 3 Through 31

A number of additional catalysts were prepared by first drying commercial zirconium hydroxide at 120 degrees Celsius for more than 5 hours. Calculated amounts of $Zn(NO_3)_2$ (from Sigma-Aldrich, more than 99.8 percent purity) were dissolved in water to form a series of clear solutions. The dried zirconium hydroxide (also from Sigma-Aldrich, more than 99.8 percent purity) was then mixed with the solutions in turn by incipient wetness, in order to form wet powders impregnated with Zn in certain proportions to the zirconium in the form of the dried zirconium hydroxide powder. The wetted powders were then dried at 80 degrees Celsius for 4 hours, followed by calcination at the temperature indicated in Table 1 below for 3 hours, to obtain a series of $Zn_xZr_yO_z$ catalysts by an incipient wetness method. These catalysts were used to convert ethanol to isobutene in the manner of Example 1. Particular reaction conditions, whether the reaction temperature, WHSV or steam to carbon ratio, for example, were varied to compare the effect on the selectivities to acetone and isobutene at full conversion of the ethanol. For several of the catalysts, some amount of sulfur was purposely doped into the catalyst to assess the effect of sulfur at those certain levels on the selectivities to acetone and to isobutene. Thus, the catalyst for example 28 was doped with 10 ppm of sulfur, while for example 29 the catalyst was doped with 50 ppm of sulfur and for example 30 with 200 ppm (by weight).

TABLE 1

Additional Ethanol to Isobutene Runs

| Ex # | Zn/Zr ratios | Calcination temp (° C.) | Reaction temp (° C.) | WHSV $g_{ethanol}/g_{catal}/hr$ | Steam to carbon ratio | Ethanol (gas wt %) | Acetone selectivity (mol %) | Isobutene selectivity (mol %) |
|---|---|---|---|---|---|---|---|---|
| 3 | 1/6.5 | 550 | 450 | 0.19 | 5 | 1.0 | 3.5 | 46.4 |
| 4 | 1/6.5 | 550 | 425 | 0.08 | 5 | 1.0 | 4.0 | 49.8 |
| 5 | 1/8 | 550 | 450 | 0.19 | 5 | 1.0 | 3.4 | 47.3 |
| 6 | 1/8 | 550 | 415 | 0.08 | 5 | 1.0 | 8.5 | 51.4 |
| 7 | 1/10 | 550 | 450 | 0.19 | 5 | 1.0 | 2.9 | 49.2 |
| 8 | 1/10 | 550 | 425 | 0.08 | 5 | 1.0 | 3.8 | 51.5 |
| 9 | 1/12 | 550 | 450 | 0.19 | 5 | 1.0 | 2.5 | 48.9 |
| 10 | 1/12 | 550 | 450 | 0.08 | 5 | 1.0 | 0.5 | 45.5 |
| 11 | 1/12 | 550 | 425 | 0.08 | 5 | 1.0 | 3.8 | 51.6 |
| 12 | 1/12 | 550 | 415 | 0.08 | 5 | 1.0 | 6.2 | 51.3 |

TABLE 1-continued

Additional Ethanol to Isobutene Runs

| Ex # | Zn/Zr ratios | Calcination temp (° C.) | Reaction temp (° C.) | WHSV $g_{ethanol}/g_{catal}/hr$ | Steam to carbon ratio | Ethanol (gas wt %) | Acetone selectivity (mol %) | Isobutene selectivity (mol %) |
|---|---|---|---|---|---|---|---|---|
| 13 | 1/14 | 550 | 450 | 0.19 | 5 | 1.0 | 4.9 | 46.8 |
| 14 | 1/10 | 500 | 450 | 0.19 | 5 | 1.0 | 0.7 | 47.6 |
| 15 | 1/10 | 500 | 475 | 0.19 | 5 | 1.0 | 0 | 41.9 |
| 16 | 1/10 | 500 | 450 | 0.08 | 5 | 1.0 | 0 | 42.7 |
| 17 | 1/10 | 500 | 425 | 0.08 | 5 | 1.0 | 1.2 | 49.3 |
| 18 | 1/10 | 600 | 475 | 0.19 | 5 | 1.0 | 7.2 | 42.3 |
| 19 | 1/10 | 600 | 450 | 0.19 | 5 | 1.0 | 13.7 | 42.1 |
| 20 | 1/10 | 600 | 450 | 0.08 | 5 | 1.0 | 4.3 | 43.8 |
| 21 | 1/10 | 600 | 425 | 0.08 | 5 | 1.0 | 12.9 | 44.8 |
| 22 | 1/10 | 600 | 400 | 0.08 | 5 | 1.0 | 32.6 | 33.1 |
| 23 | 1/10 | 650 | 450 | 0.19 | 5 | 1.0 | 32.2 | 30.1 |
| 24 | 1/10 | 650 | 450 | 0.08 | 5 | 1.0 | 10.6 | 41.8 |
| 25 | 1/10 | 650 | 425 | 0.19 | 5 | 1.0 | 44.9 | 23.0 |
| 26 | 1/10 | 650 | 425 | 0.08 | 5 | 1.0 | 26.1 | 37.4 |
| 27 | 1/10 | 650 | 415 | 0.08 | 5 | 1.0 | 34.1 | 32.3 |
| 28 | 1/10 | 550 | 415 | 0.08 | 5 | 1.0 | 7.3 | 52.1 |
| 29 | 1/10 | 550 | 415 | 0.08 | 5 | 1.0 | 6.3 | 52.4 |
| 30 | 1/10 | 550 | 415 | 0.08 | 5 | 1.0 | 8.4 | 51.2 |
| 31 | 1/8 | 550 | 450 | 0.31 | 2.5 | 15.0 | 2.8 | 53.5 |

Examples 32 Through 40

For these additional examples of converting acetic acid to isobutene, additional $Zn_xZr_yO_z$ mixed oxide catalysts were prepared both by the incipient wetness method (IW in Table 2 below) but also by the prior art hard template method (HT), and these were evaluated and the products analyzed using the same apparatus and method described above but under different sets of reaction conditions (as summarized in Table 2 below).

TABLE 2

Further Acetic acid to Isobutene Examples

| Ex # | Catalyst | Zn/Zr ratio | Reaction temp. (° C.) | WHSV $g_{acetic}/g_{catal}/hr$ | Steam to carbon ratio | $C_{G\text{-}acetic\ acid}$ (wt %) | Acetone selectivity (mol %) | Isobutene selectivity (mol %) |
|---|---|---|---|---|---|---|---|---|
| 32 | HT | 1/15 | 450 | 0.25 | 5 | 1.3 | 30.5 | 41.7 |
| 33 | HT | 1/15 | 450 | 1.14 | 5 | 1.5 | 61.1 | 18.4 |
| 34 | IW | 1/8 | 415 | 0.1 | 5 | 1.4 | 9.8 | 52.5 |
| 35 | IW | 1/10 | 415 | 0.95 | 5 | 22.3 | 50.8 | 20.1 |
| 36 | IW | 1/10 | 450 | 0.16 | 2.5 | 18.8 | 0.7 | 50.6 |
| 37 | IW | 1/10 | 450 | 0.65 | 2.5 | 18.8 | 8.3 | 46.9 |
| 38 | IW | 1/10 | 415 | 0.16 | 2.5 | 18.8 | 5.7 | 57.2 |
| 39 | IW | 1/10 | 415 | 0.33 | 2.5 | 18.8 | 16.4 | 45.3 |
| 40 | IW | 1/10 | 415 | 0.65 | 2.5 | 18.8 | 30.5 | 35.0 |

The invention claimed is:

1. A process for making isoprene, comprising:
converting acetic acid to isobutene in the presence of a $Zn_xZr_yO_z$ mixed oxide catalyst in which the ratio of x:y is from 1:100 to 10:1 and z is a stoichiometric integer for the mixed oxide catalyst; and
reacting the isobutene with formaldehyde.

2. A process comprising copolymerizing isobutene made from acetic acid in the presence of a $Zn_xZr_yO_z$ mixed oxide catalyst in which the ratio of x:y is from 1:100 to 10:1 and z is a stoichiometric integer for the mixed oxide catalyst, and isoprene prepared according to claim 1.

3. A process according to claim 1, wherein the acetic acid is obtained at least in part by fermentation of one or more of the five- and six-carbon sugars.

4. A process according to claim 1, wherein the acetic acid is obtained at least in part through an oxidative fermentation from ethanol.

5. A process according to claim 1, wherein the acetic acid is obtained at least in part by carbonylation of methanol.

6. A process according to claim 5, further comprising combining carbon dioxide and hydrogen under conditions which are effective for making at least a portion of the methanol which is carbonylated to make acetic acid.

7. A process according to either of claim 1 or 6, further comprising combining carbon dioxide and hydrogen under conditions which are effective for making methanol, and oxidizing the methanol so formed to provide at least a portion of the formaldehyde that is reacted with the isobutene.

8. A process as in claim 1, wherein the catalyst contains less than 0.14 percent by weight of sulfur.

9. A process as in claim 8, wherein the catalyst contains less than 0.01 percent by weight of sulfur.

10. A process as in claim 9, wherein the catalyst contains less than 0.001 percent by weight of sulfur.

11. A process for making isoprene, comprising:
converting acetic acid to isobutene in the presence of a $Zn_xZr_yO_z$ mixed oxide catalyst in which the ratio of x:y is from 1:100 to 10:1 and z is a stoichiometric integer for the mixed oxide catalyst;

reacting the isobutene with methanol to form biobased MTBE;

oxidatively cracking at least a portion of the biobased MTBE from acetic acid to produce isobutene and formaldehyde; and reacting the isobutene and formaldehyde to form biobased isoprene.

* * * * *